United States Patent [19]

Bair

[11] Patent Number: 4,803,226

[45] Date of Patent: Feb. 7, 1989

[54] ANTHRACENE DERIVATIVES

[75] Inventor: Kenneth W. Bair, Chapel Hill, N.C.

[73] Assignee: Burroughs Wellcome Co., Research Triangle Park, N.C.

[21] Appl. No.: 141,199

[22] Filed: Jan. 6, 1988

Related U.S. Application Data

[60] Division of Ser. No. 725,157, Apr. 22, 1985, Pat. No. 4,719,047, which is a continuation of Ser. No. 499,332, May 31, 1983, abandoned.

[51] Int. Cl.$^4$ .................. C07C 93/00; C07C 87/28; C07C 87/64
[52] U.S. Cl. .................. 514/655; 260/501.18; 564/387; 514/908
[58] Field of Search ........... 260/501.1, 501.18, 501.17, 260/501.21; 564/387, 427; 514/510, 654, 655, 766, 908

[56] References Cited

U.S. PATENT DOCUMENTS

| | | | |
|---|---|---|---|
| 4,511,582 | 4/1985 | Bair | 514/654 |
| 4,530,800 | 7/1985 | Bair | 260/501.21 |
| 4,532,344 | 7/1985 | Bair | 260/252 |
| 4,551,287 | 11/1985 | Bair | 260/501.18 |
| 4,719,046 | 1/1988 | Bair | 260/501.18 |
| 4,719,047 | 1/1988 | Bair | 260/501.18 |
| 4,719,048 | 1/1988 | Bair | 260/501.18 |
| 4,719,049 | 1/1988 | Bair | 260/501.18 |
| 4,719,055 | 1/1988 | Bair | 260/501.18 |
| 4,720,587 | 1/1988 | Bair | 564/387 |

OTHER PUBLICATIONS

Investigational New Drugs 2, 1984, Bradley et al., pp. 59–7, "The Human Tumor Colony—Forming Chemosensitivity Assay".
Dow Jones News Wire, 4/22/88, #160425-0097.

Primary Examiner—Glennon H. Hollrah
Assistant Examiner—Raymond Covington
Attorney, Agent, or Firm—Donald Brown

[57] ABSTRACT

The present invention relates to compounds of formula (I)

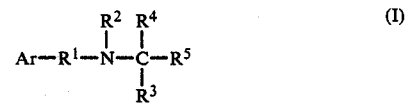

wherein
Ar is an anthracene or substituted anthracene ring system;
$R^1$ is a $C_{1-3}$ alkylene moiety;
$R^2$ is hydrogen or a $C_{1-6}$ alkyl group;
$R^3$ is a hydroxy $C_{1-6}$ alkyl group;
$R^4$ and $R^5$ are the same or different and are hydrogen, $C_{1-6}$ alkyl or hydroxy $C_{1-6}$ alkyl, esters thereof derived from condensation of carboxy acids and hydroxyl groups of $R^3$, $R^4$, and $R^5$;
Acid addition salts thereof, which have been found useful for the treatment of tumors in mammals.

7 Claims, No Drawings

ANTHRACENE DERIVATIVES

This is a divisional of co-pending application Ser. No. 725,157 filed on Apr. 22, 1985 now U.S. Pat. No. 4,719,047 which is a continuation of Ser. No. 499,332 filed May 31, 1983, now abandoned.

The present invention relates to alkanol derivatives which have been found to be inhibitors of tumor growth. More specifically the invention concerns aminoalkanol derivatives containing an anthracene or substituted anthracene ring system, methods for the synthesis thereof, pharmaceutical formulations thereof, and the use thereof as antitumor agents.

There is accordingly provided, in a first aspect, compounds of the general formula (I)

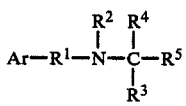

wherein

Ar is an anthracene or substituted anthracene ring system;

$R^1$ is a $C_{1-3}$ alkylene moiety;

$R^2$ is hydrogen or a $C_{1-6}$ alkyl group;

$R^3$ is a hydroxy $C_{1-6}$ alkyl group;

$R^4$ and $R^5$ are the same or different and are hydrogen, $C_{1-6}$ alkyl or hydroxy $C_{1-6}$ alkyl, esters thereof derived from condensation of carboxylic acids and hydroxyl groups of $R^3$, $R^4$, and $R^5$;

Acid addition salts thereof.

The side chain (i.e. as —$R^1$—$NR^2CR^3R^4R^5$) may be attached to the anthracene ring system at any carbon atom where attachment is possible. For example, the side chain may be attached to the 1, 2, or 9 position of an anthracenyl moiety, although attachment to other positions of the anthracene ring system is within the scope of the invention.

For antitumor activity the side chain defined by choice of $R^1$, $R^2$, $R^3$, $R^4$, and $R^5$ must not preclude in vitro intercalation by the resulting molecule of formula (I) to DNA. This property is determined using viscometric methods by the procedure of W. D. Wilson et. al., *Nucleic Acids Research* 4 2697 (1977).

In addition, the log P of the molecule as calculated by the method of C. Hansch and A. Leo in *Substituent Constants for Correlation Analysis in Chemistry and Biology*, John Wiley & Sons, New York, 1979, should normally lie in a range of acceptable values, most conveniently between −2.0 and +2.5.

$R^1$ is conveniently a straight chain $C_{1-3}$ alkylene moiety, e.g., methylene (—$CH_2$—).

$R^2$ is conveniently hydrogen but $C_{1-6}$ alkyl, e.g., methyl is also within the scope of the invention.

$R^3$ conveniently has the hydroxyl group of the hydroxyalkyl group attached to an α carbon atom (i.e. the hydroxyl group is 2 carbon atoms removed from the nitrogen atom of the side chain). For example, $R^3$ may be hydroxymethyl (—$CH_2OH$).

While $R^4$ and $R^5$ may each be hydrogen, $C_{1-6}$ alkyl, or hydroxy $C_{1-6}$ alkyl, conveniently they are alkyl or hydroxyalkyl. Most conveniently at least one of $R^4$ and $R^5$ is hydroxyalkyl. When $R^4$ and/or $R^5$ is hydroxyalkyl the hydroxyl group is conveniently on an α carbon atom, for example hydroxymethyl (—$CH_2OH$).

The preferred side chain to be attached to the anthracene ring is that derived from 2-methyl-2-amino-1,3-propanediol (II)

The anthracene ring system may optionally bear one or more substituents known in the art to be advantageous to the pharmaceutical, pharmacological, or physical properties of a therapeutic agent when attached to an aromatic nucleus. Suitable substituents include, for example, halogen (e.g. chloro, bromo), $C_{1-6}$ alkyl (e.g. methyl, ethyl), $C_{1-6}$ alkoxy (e.g. methoxy, ethoxy), halo $C_{1-6}$ alkyl (e.g. 2-chloroethyl, trifluoromethyl) $C_{1-6}$ alkylthio (e.g. thiomethyl and thioethyl), hydroxy$C_{1-6}$ alkyl (e.g., 2-hydroxyethyloxy) hydroxy $C_{1-6}$ alkylthio (e.g. 2-hydroxyethylthio), cyano, $C_{1-6}$ alkylsulphinyl, $C_{1-6}$ alkylsulphenyl; such substituents will not in general contain or comprise an aromatic moiety.

Such substituents may be attached to any appropriate position(s) on the anthracene ring.

Esters of compounds of formula (I) are conveniently those derived from $C_{1-6}$ alkanoic acids, e.g. acetic acid, propionic acid, n-butyric acid and isobutyric acid. Where the compound of formula (I) contains more than one hydroxyl group one or more of the hydroxyl groups may be esterified; however it is convenient that all hydroxyl groups are esterified.

Specific compounds within the scope of formula (I) include;

2-((9-Anthracenylmethyl)amino)-2-methyl-1,3-propanediol,
2-((1-Anthracenylmethyl)amino)-2-methyl-1,3-propanediol,
2-((10-Chloro-9-anthracenylmethyl)-amino)-2-methyl-1,3-propanediol,
2-((10-Bromo-9-anthracenylmethyl)amino)-2-methyl-1,3-propanediol,
2-Methyl-2-((10-methyl-9-anthracenylmethyl)amino)-1,3-propanediol,
2-Methyl-2-((10-methylthio-9-anthracenylmethyl)amino)-1,3-propanediol,
2-((10-(2-Chloroethyl)-9-anthracenylmethyl)amino)-2-methyl-1,3-propanediol,
2-((10-Hydroxymethyl-9-anthracenylmethyl)amino)-2-methyl-1,3-propanediol,
10-((1,1-Bis(hydroxymethyl)ethylamino)methyl)-9-anthracenecarbonitrile,
2-Methyl-2-((10-methylsulfinyl-9-anthracenylmethyl)amino)-1,3-propanediol,
2-((10-Methoxy-9-anthracenylmethyl)amino)-2-methyl-1,3-propanediol,
2-((10-Bromo-1-anthracenylmethyl)amino)-2-methyl-1,3-propanediol,
2-((4,10-Dichloro-9-anthracenylmethyl)amino)-2-methyl-1,3-propanediol,
2-((4,5-Dichloro-9-anthracenylmethyl)amino)-2-methyl-1,3-propanediol,
2-((2,10-Dichloro-9-anthracenylmethyl)amino)-2-methyl-1,3-propanediol,
2-((3,10-Dichloro-9-anthracenylmethyl)amino)-2-methyl-1,3-propanediol,
2-((10-Chloro-2,3-dimethyl-9-anthracenylmethyl)amino)-2-methyl-1,3-propanediol, 2-((4-Chloro-9-anthracenylmethyl)amino)-2-methyl-1,3-propanediol, 2-((2-Chloro-9-anthracenylmethyl)amino)-2-methyl-1,3-propanediol, 2-((10-Ethylthio-9-anthracenylmethyl)amino)-2-methyl-1,3-propanediol, 2-((10-(2-Hydroxyethylthio)-9-anthracenylmethyl)amino)-2-methyl-1,3-propanediol, 2-((2-tert-Butyl-10-chloro-9-anthracenylmethyl)amino)-2-methyl-1,3-propanediol, 2-((10-Chloro-9-anthracenylmethyl)amino)-2-hydroxymethyl-1,3-propanediol, 2-((10-(2-Hydroxyethyloxy)-9-anthracenylmethyl)amino)-2-methyl-1,3-propanediol, 2-((10-Ethoxy-9-anthracenylmethyl)amino)-2-methyl-1,3-propanediol, 2-((10-Benzoyloxy-9-anthracenylmethyl)amino)-2-methyl-1,3-propanediol, 2-((10-Butoxy-9-anthracenylmethyl)amino)-2-methyl-1,3-propanediol, 2-((10-Butyl-9-anthracenylmethyl)amino)-2-methyl-1,3-propanediol, Of these specific examples of compounds of formula (I), the most preferred compounds are 2-methyl-2-((10-methylthio-9-anthracenylmethyl)amino)-1,3-propanediol and 2-((10-(2-chloroethyl)-9-anthracenylmethyl)amino)-2-methyl-1,3-propanediol.

The compounds of formula (I) may be prepared by any method known in the art for the preparation of compounds of analogous structure. Thus the compounds of formula (I) may, for example, be prepared by any of the methods defined below.

1. Reductive amination of a compound of formula (III) with a compound of formula (IV):

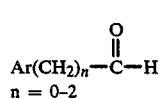
n = 0-2

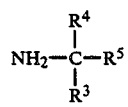

wherein Ar, $R^1$, $R^2$, $R^3$, $R^4$ and $R^5$ are as defined herein above. The conditions and reagents for such a reaction are well known in the art of organic chemistry and any such conditions/reagents may be employed. For example, sodium cyanoborohydride (NaBH$_3$CN) conveniently comprises the reducing agent, and is used according to procedures outlined by R. O. Hutchins et. al., *Organic Preparations and Procedures International* 11 201 (1979).

2. Reduction of a compound of formula (V) also formed by reaction of compounds (III) and (IV): wherein Ar, $R^1$, $R^2$, $R^3$, $R^4$, and $R^5$ are as defined above.

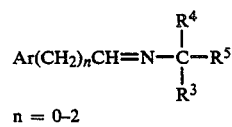
n = 0-2

The reducing agent may conveniently be LiAlH$_4$, NaBH$_4$, or hydrogen and a catalyst, or equivalent reagent as outlined by J. March, *Advanced Organic Chemistry*, 2nd ed., pages 682–683, McGraw Hill, New York, 1977. Compound (V) can also be made according to procedures outlined by J. March, vide supra page 667.

In turn, a compound of formula (III) (n=0) can be synthesized by reacting the appropriate anthracene derivative with SnCl$_4$ and Cl$_2$CHOCH$_3$ or equivalent reagents, for example, according to the method A. Rieche et. al., *Chem. Ber.* 93 88 (1960).

A compound of formula (III) (n=0) can also be synthesized by reacting the required anthracene derivative with other appropriate formylating reagents/procedures known to the art, as described by J. March vide supra pages 416–420.

Appropriately substituted anthracene rings may be converted to the corresponding aldehydes (III) (n=0–2) by any method known to the art.

Where the anthracene ring bears substituents, the appropriate compound may in turn be prepared by a variety of methods known in the art of organic chemistry depending on the nature of the substituent on the anthracene ring. For example if the substituent(s) is a halogen, the starting materials may be prepared by direct treatment of the anthracene ring with a halogenating agent (e.g. Cl$_2$, Br$_2$, or SO$_2$Cl$_2$) or indirectly by such routes as the Sandmeyer reaction (D. T. Moury, *Chem. Rev.* 42 213 (1948)). If the substituent(s) is alkyl, the anthracene may be reacted with the appropriate reagents under Friedel-Crafts reaction conditions (P. Gore, *Chem. Rev.* 55 229 (1955)).

3. Reacting a compound of formula (VI) wherein $R^3$, $R^4$, and $R^5$ are defined as above but at least one is H, and L is a leaving group as defined by J. March, vide supra pages 683 and 895, (e.g., Br, Cl, p-toluenesulfonate, etc.) with a compound of formula (VII).

wherein Ar, $R^1$ and $R^2$ are as defined above.

A compound of formula (VII) can be synthesized by the method of reductive amination described above whereby reacting a compound of formula (III), and $R^2NH_2$ (wherein $R^2$ is as defined above), in the presence of a reducing agent, for example sodium cyanoborohydride, or any other methods described in 2 or which are known to the art.

4. Reacting a compound of formula (VIII), wherein Ar, $R^1$, and L are defined $$Ar\text{—}R^1\text{—}L \qquad (VIII)$$

as above with a compound of formula (IV) as defined above.

5. Reacting a compound of formula (IX), wherein Ar is defined above

and X is a halogen or equivalent leaving group with a compound of formula (IV) as defined above (preferably with any of the hydroxy group(s) appropriately protected) followed by reduction of the resulting amide with a reducing agent such as, for example, LiAlH$_4$ or equivalent agent. The reduction may be followed by deprotection if required. The compound of formula (IX) may be prepared by any of the widely known methods in the art for preparing similar compounds.

There is therefore provided, as a further aspect of the invention, a method for the preparation of a compound of formula (I) comprising any method known for the preparation of analogous compounds, in particular, those methods defined in (1) to (5) hereinabove.

The compounds of this invention have been found to have antitumor activity. Such activity is evidenced by reduction of tumor cell number in mammals bearing ascitic tumors and their consequent increase in survival duration as compared to a control group which is untreated. Antitumor activity is further evidenced by measurable reduction in the size of solid tumors in animals following treatment of the animal with the compounds of this invention compared to the tumors of untreated control tumor-bearing animals. The murine tumor lines against which the compounds of formula (I) are active include, but are not limited to, lymphocytic leukemia P388/0, lymphocytic leukemia L1210, melanotic melanoma B16, P815 mastocytoma, and MDAY/D2 fibrosarcoma.

(As used herein "cancer" is to be taken as synonymous with "malignant tumor" or more generally "tumor" unless otherwise noted).

As has been described above, the compounds of the present invention are useful for the treatment of tumors. The invention thus further provides a method for the treatment of tumors in animals, including mammals, which comprises the administration of an effective, non-toxic amount of the compound of formula (I), an ester thereof, or an acid addition salt thereof, once, or several times a day orally, parenterally (including subcutaneous, intramuscular and intravenous), or applied topically. There is also provided as a further or alternative aspect of the invention, a compound of formula (I) for use in therapy, for example as an antitumor agent.

The amount of compound of formula (I) required to be effective as an antitumor agent will, of course, vary and is ultimately at the discretion of the medical or veterinary practitioner treating the mammal. The factors to be considered by such a practitioner (e.g., a physician) include; route of administration and pharmaceutical formulation; the mammal's body weight, surface area, age, and general condition; the particular salt or ester to be administered. However, a suitable effective antitumor dose is in the range of about 0.1 to about 120 mg/kg bodyweight, preferably in the range of about 1.5 to 50 mg/kg, e.g., 10 to 30 mg/kg. The total daily dose may be given as a single dose, multiple doses, e.g., two to six times p.d., or by intravenous infusion for any selected duration. For example, the dose range would be about 5 to 500 mg/kg per day. A typical dose for a 75 kg mammal would be about 2000 mg per day. If discrete multiple doses are indicated, treatment might typically be 500 mg of a compound of formula (I) given 4 times p.d. in the form of a tablet, capsule, liquid (e.g, syrup) or injection.

The antitumor activity of the compounds of formula (I) resides in the free base and thus the nature of the acid participating in the acid addition salts is of minor importance. However, when used in medicine, the salts of the compound of formula (I) should be both pharmacologically and pharmaceutically acceptable, but non-pharmaceutically and non-pharmacologically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids: hydrochloric, hydrobromic, sulfuric, nitric, isethionic, phosphoric, maleic, salicyclic, p-toluenesulfonic, tartaric, lactic, citric, methanesulfonic, lactobionic, formic, malonic, pantothenic, succinic, naphthalene-2-sulfonic and benzenesulfonic.

While it is possible for the active compound (defined herein as compound of formula (I) to be administered alone as the raw chemical, it is preferable to present the active compound as a pharmaceutical formulation. Formulations of the present invention, for medical use, comprise the active compound together with one or more pharmaceutically acceptable carriers thereof and optionally any other therapeutic ingredients. The carrier(s) must be pharmaceutically acceptable in the sense of being compatible with the other ingredients of the formulation and not deleterious to the recipient thereof.

The present invention therefore further provides a pharmaceutical formulation comprising a compound of formula (I) or an ester thereof (in the form of the free base or a pharmaceutically acceptable acid addition salt) together with a pharmaceutically acceptable carrier.

There is also provided a method for the preparation of pharmaceutical formulation which comprises bringing into association a compound of formula (I) or an ester thereof and a pharmaceutically acceptable carrier thereof.

The formulations include those suitable for oral, rectal, or parenteral (including subcutaneous, intramuscular, and intravenous injection) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into desired formulations.

Formulations of the present invention suitable for oral administration may be presented as discrete units such as capsules, cachets, tablets, or lozenges, each containing a predetermined amount of the active compound; as a powder or granules; or a suspension in an aqueous liquid or non-aqueous liquid such as a syrup, an elixir, an emulsion, or a draught. The active compound may also be presented as a bolus, electuary, or paste.

A tablet may be made by compression or molding, optionally with one or more accessory ingredients. Compressed tablets may be prepared by compressing in a suitable machine, the active compound in a free-flowing form such as a powder or granules, optionally mixed with a binder, lubricant, inert diluent, surfactant, or dispersing agent. Molded tablets may be made by molding in a suitable machine, a mixture of the powdered active compound with any suitable carrier.

A syrup may be made by adding the active compound to a concentrated, aqueous solution of a sugar for example sucrose to which may also be added any accessory ingredient. Such accessory ingredient(s) may include flavorings, an agent to retard crystallization of the sugar or an agent to increase the solubility of any other ingredient, such as a polyhydric alcohol (e.g. glycerol or sorbitol).

Formulations for rectal administration may be presented as a suppository with a usual carrier such as cocoa butter.

Formulations suitable for parenteral administration conveniently comprise a sterile aqueous preparation of the active compound which is preferably isotonic with the blood of the recipient.

In addition to the aforementioned ingredients, the formulations of this invention may further include one or more accessory ingredient(s) selected from diluents, buffers, flavoring agents, binders, surface active agents, thickeners, lubricants, preservatives (including antioxidants) and the like.

The following examples are provided by way of illustration of the present invention and should in no way be construed as a limitation thereof.

GENERAL COMMENTS

All solvents were reagent grade and used without further purification with the following exceptions. THF was dried by distillation from Na/K alloy under $N_2$ and used immediately. Toluene ($PhCH_3$) was distilled from $CaH_2$ under $N_2$ and stored over 3 Å molecular sieves. Chemicals used were reagent grade and used without purification unless noted. The full name and address of the suppliers of the reagents and chemicals is given when first cited. After this, an abbreviated name is used.

Preparative HPLC was carried out on a Water's Prep LC/System 500A machine using two 500 g silica gel ($SiO_2$) cartridges unless otherwise noted. Plugs of $SiO_2$ used for purifications were "flash chromatography" silica gel (E. Merck, silica gel 60, 230–400 mesh). An appropriate volume sintered glass funnel was filled approximately ¾ full with the $SiO_2$ and packed evenly by tapping the outside of the funnel. A piece of filter paper was then placed on top of the $SiO_2$ and a solution of the material to be purified applied evenly to the top. Gentle suction through a filter flask moved the eluting solvent through the plug rapidly. The appropriate size fractions were combined as needed and further manipulated.

General procedures are described in detail. Analogous procedures show melting point (mp), recrystallization solvents, and elemental analyses (all elements analyzing within a difference of ≦0.4% of the expected value). Any changes to the procedure such as solvent, reaction temperature, reaction time, or workup are noted.

NMR ($^1H$, $^{13}C$), IR, MS data of all new products were consistent with the expected and proposed structures. The positions assigned to structural isomers were unequivocally determined by a number of NMR techniques. All final products were dried in a vacuum oven at 20 mm Hg pressure at the temperature indicated overnight (12–16 h). All temperatures are in degrees Celsius.

EXAMPLE 1

2-((9-Anthracenylmethyl)amino)-2-methyl-1,3-propanediol hydrochloride

To a 2 L Erlenmeyer flask was added 9-anthracenecarbaldehyde (Aldrich Chemical Co., Milwaukee, WI, 53201, 20.63 g, 0.1 mol) 2-methyl-2-amino-1,3-propanediol (Aldrich, 9.13 g, 86.8 mmol), p-toluenesulfonic acid.$H_2O$ (Eastman Kodak Co., Rochester, NY, 14650, 0.1 g, 0.5 mmol), and $PhCH_3$ (500 mL). The mixture was warmed to reflux for a few minutes and $H_2O$ (2–3 mL) was driven off. The resulting golden colored solution was allowed to cool to RT, diluted with absolute EtOH (500 mL) and stirred overnight. $NaBH_3CN$ (Aldrich, 95%, 2.51 g, 42 mmol) was added to the reaction. After the $NaBH_3CN$ dissolved, an indicator (bromocresol green, Eastman, 5 mg) was added. To the resulting blue solution was added 5 drops of 1M solution of HCl gas in absolute EtOH every 15 minutes. After 3 days the indicator turned green then yellow and voluminous white precipitate was present in the flask. To the flask was then added 1M HCl gas (10 mL) in absolute EtOH. The reaction was diluted to 4 L with $Et_2O$ and stirred for 1 h. The precipitate was then collected by filtration through a medium porosity glass fritted funnel and pressed dry. The filter cake was washed with $CH_2Cl_2$ (4×500 mL), pressed and sucked dry, and dried (100°). The crude solid was recrystallized from EtOH/$Et_2O$ (3×) to give 13.44 g (40%) of 2-((9-anthracenylmethyl)amino)-2-methyl-1,3-propanediol hydrochloride mp 139°–140° (dec), (C, H, Cl, N).

EXAMPLE 2

2-((1-Anthracenylmethyl)amino)-2-methyl-1,3-propanediol hydrochloride

A. 9,10-Dihydro-9,10-dioxo-1-anthracenecarboxylic acid

Benzanthrone (Aldrich, technical grade) was purified by chromatography on a plug of $SiO_2$ with $PhCH_3$ as eluent (83% recovery). mp 172°–172.5° (lit. mp 170°–171°, O. Bally and R. Scholl, Ber. 44 1656 (1911)).

The purified benzanthrone (63.7 g, 0.277 mol) was dissolved in 1500 mL of glacial HOAc at 90° and stirred with a mechanical stirrer. After cooling to 80° solid $CrO_3$ (Mallinckrodt, Co., 2nd and Mallinckrodt St., St. Louis, MO, 63147, 200 g, 2 mol) was added in ~5 g portions over about 4 h. The exothermic reaction maintained the mixture at ~80° during this time and $CO_2$ was evolved. After $CO_2$ evolution ceased and the reaction temperature fell, the heating mantle was reapplied and the reaction stirred at 75° for an additional 6 h. The reaction was cooled to RT and stirred overnight. $H_2O$ (1.5 L) was then added to the dark-green solution. The reaction was then filtered to give a deep brown solid which was washed with $CH_3OH$ (200 mL) until the washings were colorless. The resulting solid was dissolved 2 L of hot methoxyethanol and filtered through Celite (Trade Mark of Johns-Manville Co., Denver, CO, 80110) to remove a black solid residue. The volume of the solution was reduced to ~75 mL (some solid formed) and diluted with 100 mL $CH_3OH$ to give the product. This material was filtered to give 32.0 g (46%) of golden brown 9,10-dihydro-9,10-dioxo-1-anthracenecarboxylic acid mp 287°–289°, (C, H,), (lit. mp 293°–294°, *Chemistry of Carbon Compounds* IIIb, edited by E. H. Rodd, 1419 (1956), Elsevier, N.Y.).

B. 1-Anthracenecarboxylic acid

To a 5 L 3-neck flask fitted with condenser, thermometer, and overhead stirrer was added 9,10-dihydro-9,10-dioxo-1-anthracenecarboxylic acid (90 g, 0.357 mol), Zn dust (Mallinckrodt, 250 g, 3.82 mol), $CuSO_4.5H_2O$ (Mallinckrodt, 5 g), and 28% $NH_4OH$ (Mallinckrodt, 2500 mL). The mixture was heated slowly until a dark-red solution occurred as the temperature reached 85°. After 3.5 h the color of the solution faded to yellow. The reaction was heated an additional 1 h, and then cooled and the excess Zn filtered. The filter cake was washed with more NH₄OH (100 mL) and then discarded. The filtrate was carefully acidified to pH 1 with conc. HCl added in portions over 1 h affording a light-green precipitate which was separated by filtration. The solid was washed with H₂O (200 mL) and then recrystallized once from methoxyethanol/H₂O (with a small amount of HCl) to give 65 g (82%) filtered, and dried at 75° of 1-anthracenecarboxylic acid mp 249°–250°, (C, H), (lit. mp 245°, *Chemistry of Carbon Compounds* IIIb, edited by E. H. Rodd, 1373 (1956), Elsevier, N.Y.).

C. (1-Anthryl)methanol

To a 500 mL 2-neck flask equipped with condenser, addition funnel with N₂ inlet, and stirring bar was added 1-anthracenecarboxylic acid (6.88 g, 31 mmol) and dry THF (250 mL). To the addition funnel, was added a 1M solution of BH₃ in THF (Aldrich, 50 mL, 50 mmol) via cannula. The BH₃ solution was added over 1 h and the solution stirred overnight at RT. CH₃OH was then added until H₂ evolution ceased. H₂O (5 mL) and then 1N HCl (5 mL) was added to the flask. The solvents were removed and then PhCH₃ (100 mL) added to the flask. The PhCH₃ was then also removed. The resulting solid was recrystallized from EtOAc/hexane to give 4.3 g (67%) of (1-anthryl)methanol mp 124°–125°, (C, H), (lit. 124°–125°, S. Akiyama et. al., *Bull. Chem. Soc. Jap.* 35 1826 (1962)).

D. 1-Anthracenecarbaldehyde

To a 2 L round bottom flask equipped with condenser and magnetic stirring bar was added (1-anthryl)methanol (21.0 g, 0.10 mol), CH₂Cl₂ (1200 mL) and pyridinium chlorochromate (Aldrich, 32.33 g, 0.15 mol). The mixture was then refluxed for 5 h. The reaction was cooled and then filtered through 400 g plug of silica gel using PhCH₃ as eluting solvent. The first 1 L of solution was collected and concentrated to give 16 g of crude product. This material was purified by preparative HPLC using PhCH₃ as eluting solvent. The solvent was removed and the pure material recrystallized from PhCH₃/hexane to give 14.0 g (67%) of 1-anthracenecarbaldehyde mp 130°–131.5°, (C, H), (lit. mp 126.5°–127.5°, P. H. Gore *J. Chem. Soc.* 1616 (1959)).

E.
2-((1-Anthracenylmethyl)amino)-2-methyl-1,3-propanediol hydrochloride

Using the reductive amination procedure outlined in 1, 1-anthracenecarbaldehyde and 2-methyl-2-amino-1,3-propanediol gave 2-((1-anthracenylmethyl)amino)-2-methyl-1,3-propanediol hydrochloride mp 189°–191° (dec), (EtOH/Et₂O), (C, H, Cl, N).

EXAMPLE 3

2-((10-Chloro-9-anthracenylmethyl)amino)-2-methyl-1,3-propanediol hydrochdloride Using the reductive animation procedure outlined in 1, 10-chloro-anthracene-9-carbaldehyde (Aldrich) and 2-amino-2-methyl-1,3-propanediol (Aldrich) gave 2-((10-chloro-9-anthracenylmethyl)amino)-2-methyl-1,3-propanediol hydrochloride mp 268°–269° (dec), (CH₃OH/Et₂O), (C, H, Cl, N).

EXAMPLE 4

2-((10-Bromo-9-anthracenylmethyl)amino)-2-methyl-1,3-propanediol hydrochloride

A. 10-Bromo-9-anthracenecarbaldehyde

This material was made from 9,10 dibromoanthracene (Eastman, 20 g, 60 mmol) modifying the procedure of R. Kuhn and H. Fischer, *Chem. Ber.* 94 3060 (1961). In this procedure, the reaction mixture was cooled to −78° before the nBuLi was added. The resulting mixture was warmed to RT over 1 H and then refluxed until the crystalline starting material disappeared. The mixture was then cooled to −78° again before the DMF was added (in one portion). The flask was warmed to RT and then quenched with 1M HBr (200 mL). The two-phase system was then extracted with CH₂Cl₂ (3×500 mL). The extracts combined, dried (MgSO₄), filtered, and the solvent removed to give the crude material. This was purified by preparative HPLC using PhCH₃ as the eluting solvent. After the solvent was removed 13.06 g (76%) of 10-bromo-9-anthracenecarbaldehyde mp 215°–216.5°, lit. mp 218°, P. Kuhn and H. Fischer, *Chem. Ber.* 94 3060 (1961)), (C, H, Br) was obtained.

B.
2-((10-Bromo-9-anthracenylmethyl)amino)-2-methyl-1,3-propanediol hydrochloride Using the reductive amination procedure outlined in 1, 10-bromoanthracene-9-carbaldehyde and 2-methyl-2-amino-1,3-propanediol (Aldrich) gave 2-((10-bromo-9-anthracenylmethyl)amino)-2-methyl-1,3-propanediol hydrochloride mp 263°–264° (dec), (CH₃OH/Et₂O), (C, H, Br, Cl, N).

EXAMPLE 5

2-Methyl-2-((10-methyl-9-anthracenylmethyl)amino)-1,3-propanediol hydrochloride

Using the reductive amination procedure outlined in 1, 10-methyl-9-anthracenecarbaldehyde (Aldrich) and 2-methyl-2-amino-1,3-propanediol (Aldrich) gave 2-methyl-2-((10-methyl-9-anthracenylmethyl)amino)-1,3-propanediol hydrochloride.½H₂O mp >300°, (EtOH/Et₂O), (C, H, Cl, N).

EXAMPLE 6

2-Methyl-2-((10-methylthio-9-anthracenylmethyl)amino)-1,3-propanediol hydrochloride 10-Methylthio-9-anthracenecarbaldehyde The procedure of V. Rogovik et. al., *Zh. Org. Khim.* 3 1315 (1969) was modified in the following way: A 2 L 3-neck flask fitted with stirring bar, condenser, addition funnel, thermometer, N₂ inlet, and bubbler was charged with 10-chloro-9-anthracenecarbaldehyde (Aldrich, 28.0 g, 0.116 mol), and DMF (Aldrich, 1 L). The solid dissolved when the reaction mixture was warmed to 60°. The addition funnel was filled with a solution of Na₂S (Mallinckrodt, 28 g, 0.116 mol) in 30 mL of H₂O. This solution was added rapidly to the flask causing a considerable amount of spattering as the purple thiolate formed. The reaction mixture was stirred at 65° for 45 minutes, then cooled to 30° (ice bath). CH₃I (Aldrich, 27.36 g, 0.193 mol) was then added to the flask dropwise over 5 minutes. The color of the solution changed from deep purple to yellow after 3 h. After 15 minutes, 1 L of H₂O was added to the reaction mixture. The yellow solid that formed was collected by filtration, dissolved in hot PhCH₃, (500 mL) dried (MgSO₄), and filtered through Celite (Trade Mark). Most of the volume of PhCH₃ was removed and the resultant oil swirled with hexane (200 mL) to give a bright yellow solid. The material was dried at 50° affording 25.04 g (86%) of 10-methylthio-9-anthracenecarbaldehyde mp 98.5°–99°, (C, H, S).

B.
2-Methyl-2-((10-methylthio-9-anthracenylmethyl)amino)-1,3-propanediol hydrochloride Using the reductive amination procedure outlined in 1, 10-methylthioanthracene-9-carbaldehyde and 2-methyl-2-amino-1,3-propanediol (Aldrich) gave 2-methyl-2-((10-methylthio-9-anthracenylmethyl)amino)-1,3-propanediol hydrochloride mp 225°–226° (dec), (EtOH/Et₂O), (C, H, Cl, N, S).

EXAMPLE 7

2-((10-(2-Chloroethyl)-9-anthracenylmethyl)amino)-2-methyl-1,3-propanediol hydrochloride A. 10-(2-Chloroethyl)-9-anthracenecarbaldehyde Using the Vilsmeier procedure (L. F. Fieser, *Org. Syn. Coll. Vol.* III, 98 (1955)), 9-vinylanthracene (Aldrich) gave 10-(2-chloroethyl)-9-anthracenecarbaldehyde mp 158°–159°, (PhCH₃/CH₃OH), (C, H, Cl).

B.
2((10-(2-Chloroethyl)-9-anthracenylmethyl)amino)-2-methyl-1,3-propanediol hydrochloride Using the reductive amination procedure outlined in 1, 10-(2-chloroethyl)-9-anthracenecarbaldehyde and 2-methyl-2-amino-1,3-propanediol (Aldrich) gave 2-((10-(2-chloroethyl)-9-anthracenylmethyl)amino)-2-methyl-1,3-propanediol hydrochloride mp 229°–231° (dec), (EtOH/Et₂O), (C, H, Cl, N).

EXAMPLE 8

2-((10-Hydroxymethyl-9-anthracenylmethyl)amino)-2-methyl-1,3-propanediol hydrochloride Using the reductive amination procedure outlined in 1, 10-hydroxymethyl-9-anthracenecarbaldehyde (made by the method of Y. Lin et. al., *J. Org. Chem.* 44 4701 (1979)) and 2methyl-2-amino-1,3-propanediol (Aldrich) gave 2-((10-hydroxymethyl-9-anthracenylmethyl)amino)-2-methyl-1,3-propanediol hydrochloride.¼H₂O mp 209°–210° (dec), (EtOH/Et₂O), (C, H, Cl, N).

EXAMPLE 9

10-((1,1-Bis(hydroxymethyl)ethylamino)methyl)-9-anthracene carbonitrile hydrochloride A. 10-Formyl-9-anthracenecarbonitrile A 250 mL 2-neck round bottom flask fitted with thermometer, condenser, N₂ inlet and bubbler, and stirring bar was charged with 10-chloro-9-anthraldehyde (Aldrich, 5 g, 21 mmol), CuCN (Fisher Scientific Company, 711 Forbes Ave., Pittsburgh, PA, 15219, 2.14 g, 24 mmol), N-methylpyrrolidinone (100 mL), DMF (15 mL), and bis(triphenylphosphine)palladium dichloride (Fluka, 0.08 g, 0.1 mmol). The mixture was warmed to 170° and stirred 15 h under N₂. After 1.5 h, the mixture became homogeneous. The reaction was cooled to 70° and poured into a solution composed of 16 g of FeCl₃·6-H₂O, (Mallinckrodt), 70 mL of 1.0M HCl and 400 mL H₂O. The resulting mixture was stirred at 60°–70° for 1 h, filtered and a crude orange solid isolated. This material was dissolved in 1 L of hot PhCH₃ and passed through a small plug (100 g) of SiO₂. The filtrate was then concentrated to 75 mL and diluted with hexane (200 mL). The orange solid which formed was collected by filtration and dried at 50° to give 3.17 g (68%) of 10-formyl-9-anthracenecarbonitrile mp 270°–275°, (C, H, N).

B.
10-((1,1-Bis(hydroxymethyl)ethylamino)methyl)-9-anthracenecarbonitrile hydrochloride Using the reductive amination procedure outlined in 1, 10-formyl-9-anthracene-carbonitrile and 2-methyl-2-amino-1,3-propanediol (Aldrich) gave 10-((1,1-Bis(hydroxymethyl)ethylamino)methyl)-9-anthracenecarbonitrile hydrochloride mp 307°–308°, (CH₃OH/Et₂O), (C, H, Cl, N).

EXAMPLE 10

2-Methyl-2-((10-methylsulfinyl-9-anthracenylmethyl)amino)-1,3-propanediol hydrochloride A. 10-Methylsulfinyl-9-anthracenecarbaldehyde A 1 L round bottom flask fitted with addition funnel and stirring bar was charged with 10-methylthio-9-anthracenecarbaldehyde (example 6A, 12.0 g, 48 mmol) and 450 mL of CH₂Cl₂. The resulting solution was cooled to 5° with an ice bath. A solution of MCPBA (Aldrich (85%), 9.64 g, 48 mmol) in 350 mL of CH₂Cl₂ was then added dropwise to the flask over 1 h. The reaction mixture was allowed to warm to RT over 1 h and then was washed with 5% NaHCO₃ solution (2×500 mL), dried (Na₂SO₄), filtered, concentrated to 500 mL, and passed through SiO₂ (250 g) using PhCH₃ (5 L) eluting solvent. The desired material was then eluted from the SiO₂ using EtOAc (2 L) as the eluting solvent. The solvent volume was reduced to 100 mL and then diluted to 700 mL with hexane. The resulting yellow solid was filtered and dried at 50° to give 11.98 g (94% of 10-methylsulfinyl-9-anthracenecarbaldehyde mp 182°–184°, (C, H, S).

B.
2-Methyl-2-((10-methylsulfinyl-9-anthracenylmethyl)amino)-1,3-propanediol hydrochloride Using the reductive amination procedure outlined in 1, 10-methylsulfinyl-9-anthracenecarbaldehyde and 2-methyl-2-amino-1,3-propanediol (Aldrich) gave 2-methyl-2-((10-methylsulfinyl-9-anthracenylmethyl)amino)-1,3-propanediol hydrochloride mp 266°–268° (dec), (EtOH/Et₂O), (C, H, Cl, N, S).

EXAMPLE 11

2-((10-Methoxy-9-anthracenylmethyl)amino)-2-methyl-1,3-propanediol hydrochloride A. 10-Methoxy-9-anthracenecarbaldehyde A 2 L round bottom flask fitted with distilling head, thermometer, and condenser was charged with 15-crown-5 (Aldrich, 25.89 g, 0.118 mol), NaOCH₃ (Aldrich, 7.62 g, 0.141 mol), and CH₃OH (50 mL). After 5 minutes 10-chloro-9-anthracenecarbaldehyde (Aldrich, 28.4 g, 0.118 mol) and 900 mL of dry PhCH₃ were added to the clear colorless solution. The solvent was distilled off until the head temperature reached 108°

(300 mL). Additional dry PhCH₃ was added to give at total of 1 L volume. The reaction mixture was refluxed for 4 h, cooled and poured onto a large plug of SiO₂ (1000 g) in a sintered glass funnel. The crude product was chromatographed using PhCH₃ as eluent (5 L). The fractions (250 mL) containing the product were combined (~3 L) and the solvent volume reduced to 500 mL. The shiny golden crystals which formed were filtered and drying at 50° 15.6 g of material. The volume of the filtrate was reduced to 200 mL and more material fell out of solution and was filtered and dried to give 6.91 g of additional material. The two crops were combined to give 22.51 g (81%) of 10-methoxy-9-anthracenecarbaldehyde which was used without further purification. Recrystallization gave analytically pure material mp 164.5°–166.5°, (PhCH₃), (C, H), (lit. mp 165°, J. B. Conant and M. Bramann, *J. Amer. Chem. Soc.* 50 2305 (1928)).

B.
2-((10-Methoxy-9-anthracenylmethyl)amino)-2-methyl-1,3-propanediol hydrochloride Using the reductive amination procedure outlined in 1, 10-methoxy-9-anthracenecarbaldehyde and 2-methyl-2-amino-1,3-propanediol (Aldrich) gave 2-((10-methoxy-9-anthracenylmethyl)amino)-2-methyl-1,3-propanediol hydrochloride mp 173°–174° (dec), (EtOH/Et₂O), (C, H, Cl, N).

EXAMPLE 12

2-((10-Bromo-1-anthracenylmethyl)amino)-2-methyl-1,3-propanediol hydrochloride

A. (10-Bromo-1-anthryl)methanol

10-Bromo-1-anthracenecarboxylic acid made from example 2B by the procedure of E. Barnett, J. W. Cook, and H. H. Grainger, *Ber.* 57 B, 1775 (1924), was reduced with BH₃ in THF by the procedure outlined in 2C to give (10-bromo-1-anthryl)methanol mp 125°–127°, (EtOAc/hexane), (C, H, Br).

B. 10-Bromo-1-anthracenecarbaldehyde

Using the procedure outlined in 2D, oxidation of (10-bromo-1-anthryl)-methanol with PCC gave 10-bromo-1-anthracenecarbaldehyde mp 134.5°–135.5°, (PhCH₃/hexane), (C, H, Br).

C.
2-((10-Bromo-1-anthracenylmethyl)amino)-2-methyl-1,3-propanediol hydrochloride Using the reductive amination procedure outlined in 1, 10-bromo-9-anthracenecarbaldehyde and 2-methyl-2-amino-1,3-propanediol (Aldrich) gave 2-((10-bromo-1-anthracenylmethyl)amino)-2-methyl-1,3-propanediol hydrochloride mp 225°–226.5° (dec), (EtOH/Et₂O), (C, H, Br, Cl, N).

EXAMPLE 13

2-((4,10-Dichloro-9-anthracenylmethyl)amino)-2-methyl-1,3-propanediol hydrochloride A. 1,10-Dichloro-9-anthracenecarbaldehyde and 4,10-Dichloro-9-anthracenecarbaldehyde Using the procedure of V. I. Rogovik et. al., *Zh. Org. Khim.* 3 1315 (1967), 1-chloroanthraquinone (Aldrich) gave a mixture of 1,10- and 4-10-dichloro-9-anthracenecarbaldehydes. These compounds were separated by preparative HPLC using PhCH₃ as the eluting solvent and employing the shave/recycle technique to give 3.05 g (14%) of 1,10-dichloro-9-anthracenecarbaldehyde mp 180.5°–183°, (Rf=0.64, SiO₂, PhCH₃), (C, H, Cl), and 0.59 g (3%) of 4,10-dichloro-9-anthracenecarbaldehyde mp 167°–170°, (Rf=0.57, SiO₂, PhCH₃), (C, H, Cl). Later preparations were more successful when the reaction was run at 95° for the 4 h reaction time rather than increasing the reaction temperature to 125° for the last 2 h period.

B.
2-((4,10-dichloro-9-anthracenylmethyl)amino)-2-methyl-1,3-propanediol hydrochloride Using the reductive amination procedure outlined in 1, 4,10-dichloro-9-anthracenecarbaldehyde and 2-methyl-2-amino-1,3-propanediol (Aldrich) gave 2-((4,10-dichloro-9-anthracenylmethyl)amino)-2-methyl-1,3-propanediol hydrochloride mp 261°–262° (dec.), (EtOH/Et₂O), (C, H, Cl, N).

Example 14

2-((4,5-Dichloro-9-anthracenylmethyl)amino)-2-methyl-1,3-propanediol hydrochloride A. 4,5-Dichloro-9-anthracenecarbaldehyde 1,8-Dichloroanthracene prepared by the method of H. O. House et. al. (*J. Org. Chem.* 38 1167 (1973)). A 3 L 3-neck flask fitted with overhead mechanical stirrer, thermometer, condenser, and N₂ line was charged with 1,8-dichloroanthracene (17.3 g, 70 mmol) and CH₂Cl₂ (1500 mL). After further cooling with salt-ice bath to 5°, SnCl₄ (Aldrich, 98%, 36.5 g, 0.14 mol, 16.4 mL), was added in one portion to the reaction. No temperature change occurred. The pot temperature was kept below 5°, and 1,1-dichloromethylmethylether (Aldrich, 16.09 g, 0.14 mol, 12.60 mL) was added dropwise over 1 h. The resulting suspension was warmed slowly to reflux (37°). Considerable HCl gas evolution occurred during the warming and the early part of the reaction at 37°. The reaction mixture was then cooled to 10° and hydrolysed by careful addition of 1 L of cold H₂O. After 4 h the layers were separated and the organic layer filtered, dried with anhydrous Na₂SO₄ (Mallinckrodt, 100 g) and filtered again and the volume reduced to 100 mL. The clear yellow solution was passed through a 1000 g plug of SiO₂ using PhCH₃ as the eluting solvent with 500 mL fractions. This chromatography separated unreacted 1,8-dichloroanthracene (11 g, 63%) from the aldehyde and a more polar product. Fractions containing the aldehyde were combined and the PhCH₃ removed, to give 5.83 g (21%) of 4,5-dichloro-9-anthracenecarbaldehyde mp 218°–220°, (PhCH₃/CH₃OH), (C, H, Cl), (lit. 224°–226°, E. L. Stogryn, *J. Med. Chem.* 17 563 (1974)).

B.
2-((4,5-Dichloro-9-anthracenylmethyl)amino-2-methyl-1,3-propanediol hydrochloride Using the reductive amination procedure outlined in 1, 4,5-dichloro-9-anthracenecarbaldehyde and 2-methyl-2-amino-1,3-propanediol (Aldrich) gave 2-((4,5-dichloro-9-anthracenylmethyl)amino)-2-methyl-1,3-propanediol hydrochloride mp 239.5°–240.5° (dec), (EtOH/Et₂O), (C, H, Cl, N).

EXAMPLE 15

2-((2,10-Dichloro-9-anthracenylmethyl)amino)-2-methyl-1,3-propanediol hydrochloride

EXAMPLE 16

2-((3,10-Dichloro-9-anthracenylmethyl)amino)-2-methyl-1,3-propanediol hydrochloride A. 2,10-Dichloroanthracenecarbaldehyde and 3,10-dichloro-9-anthracene carbaldehyde Using the procedure of V. I. Rogovik et. al. (*Zh. Org. Khim.* 3, 1315 (1967)) 2-chloroanthraquinone (Aldrich) gave a mixture (~1:1) of 2,10- and 3,10-dichloroanthracenecarbaldehydes (68%). A portion of the mixture was separated by preparative HPLC using the shave/recycle technique to give 2,10-dichloro-9-anthracenecarbaldehyde mp 175.5°–176.5°, (PhCH$_3$), (C, H, Cl), and 3,10-dichloro-9-anthracenecarbaldehyde mp 173.5°–175°, (PhCH$_3$), (C, H, Cl). The remainder of the material was used as a mixture.

B.
2-((2,10-Dichloro-9-anthracenylmethyl)amino)-2-methyl-1,3-propanediol hydrochloride 2-((3,10-Dichloro-9-anthracenylmethyl)amino)-2-methyl-1,3-propanediol hydrochloride Using the reductive amination procedure outlined in 1, the mixture of 2,10- and 3,10-dichloro-9-anthracenecarbaldehydes and 2-methyl-2-amino-1,3-propanediol gave after workup a mixture of 2-((2,10- and 3,10-dichloro-9-anthracenylmethyl)amino)-2-methyl-1,3-propanediols. These two compounds were separated by preparative HPLC using EtOAc as eluting solvent and the recycle technique to give after treatment with gaseous HCl in EtOH 2-((2,10-dichloro-9-anthracenylmethyl)amino)-2-methyl-1,3-propanediol hydrochloride mp 305°–306° (dec), (CH$_3$OH/Et$_2$O), (C, H, Cl, N), (Rf=0.53, SiO$_2$, EtOAc) and 2-((3,10-dichloro-9-anthracenylmethyl)amino)-2-methyl-1,3-propanediol hydrochloride, mp 303°–304° (dec), (CH$_3$OH/Et$_2$O), (C, H, Cl, N), (Rf=0.39, SiO$_2$, EtOAc).

EXAMPLE 17

2-((10-Chloro-2,3-dimethyl-9-anthracenylmethyl)amino)-2-methyl-1,3-propanediol hydrochloride A. 10-Chloro-2,3-dimethyl-9-anthracenecarbaldehyde 2,3-Dimethylanthraquinone prepared by the procedure of C. F. Allen and A. Bell, *Org. Syn. Coll.* Vol. III, 310 (1955), was treated with Fe/POCl$_3$/DMF using the procedure of V. I. Rogovik et. al., *Zh. Org. Khim.* 3 1315 (1967) to give 10-chloro-2,3-dimethyl-9-anthracenecarbaldehyde mp 150°–153°, (PhCH$_3$/MeOH), (C, H, Cl).

B.
2-((10-Chloro-2,3-dimethyl-9-anthracenylmethyl)amino)-2-methyl-1,3-propanediol hydrochloride Using the reductive amination procedure outlined in 1, 10-chloro-2,3-dimethyl-9-anthracenecarbaldehyde and 2-methyl-2-amino-1,3-propanediol (Aldrich) gave 2-((10-chloro-2,3-dimethyl-9-anthracenylmethyl)amino)-2-methyl-1,3-propanediol hydrochloride mp 251°–252° (dec), (CH$_3$OH/Et$_2$O), (C, H, Cl, N).

EXAMPLE 18

2-((4-Chloro-9-anthracenylmethyl)amino)-2-methyl-1,3-propanediol hydrochloride

A. 4-Chloro-9-anthracenecarbaldehyde

1-Chloroanthracene prepared from 1-chloroanthraquinone (Aldrich) by the method of H. O. House et. al. (*J. Org. Chem.* 38 1167 (1973)) was formylated by the procedure outlined in 14A to give 4-chloro-9-anthracenecarbaldehyde mp 129°–131°, (PhCH$_3$/CH$_3$OH), (C, H, Cl).

B.
2-((4-Chloro-9-anthracenylmethyl)amino)-2-methyl-1,3-propanediol

Using the reductive amination procedure outlined in 1, 4-chloro-9-anthracenecarbaldehyde and 2-methyl-2-amino-1,3-propanediol (Aldrich) gave 2-((2-chloro-9-anthracenylmethyl)amino)-2-methyl-1,3-propanediol hydrochloride, mp 225°–226° (dec), (EtOH/Et$_2$O), (C, H, Cl, N).

EXAMPLE 19

2-((2-Chloro-9-anthracenylmethyl)amino)-2-methyl-1,3-propanediol hydrochloride

A. 2-Chloro-9-anthracenecarbaldehyde and 3-chloro-9-anthracenecarbaldehyde

2-Chloroanthracene prepared from 2-chloroanthraquinone (Aldrich) by the method of H. O. House et. al. (*J. Org. Chem.* 38 1167 (1973)) was formylated by the procedure outlined in 14A to give a (4:1) mixture of 2- and 3-chloro-9-anthracenecarbaldehydes (87%). Trituration of the material with CH$_3$OH gave preferential crystallization of 2-chloro-9-anthracenecarbaldehyde which after further crystallization (PhCH$_3$/hexane) gave the pure 2-isomer mp 149°–150° (C, H, Cl) (lit. 148°–150°, British Patent No. 1,149,557). The filtrate (Rf=0.59, SiO$_2$, PhCH$_3$) from the CH$_3$CH trituration was further purified by preparative HPLC to give pure 3-chloro-9-anthraldehyde mp 122°–123.5°, (PhCH$_3$/hexane), (C, H, Cl), (Rf=0.48, SiO$_2$, PhCH$_3$).

B.
2-((2-Chloro-9-anthracenylmethyl)amino)-2-methyl-1,3-propanediol hydrochloride Using the reductive amination procedure outlined in 1, 2-chloro-9-anthracenecarbaldehyde and 2-methyl-2-amino-1,3-propanediol gave 2-((2-chloro-9-anthracenylmethyl)amino-2-methyl-1,3-propanediol hydrochloride mp 265°–266° (dec), (CH$_3$OH/Et$_2$O), (C, H, Cl, N).

EXAMPLE 20

2-((10-Ethylthio-9-anthracenylmethyl)amino)-2-methyl-1,3-propanediol hydrochloride A. 10-Ethylthio-9-anthracenecarbaldehyde Using the procedure described in 6A, 10-chloro-9-anthracenecarbaldehyde (Aldrich) and ethyl iodide (Fisher) gave an oil which solidifed to give 10-ethylthio-9-anthracencarbaldehyde mp 74°–75.5° (C, H, S).

B.
2-((10-Ethylthio-9-anthracenylmethyl)amino)-2-methyl-1,3-propanediol hydrochloride Using the reductive amination procedure outlined in 1, 10-ethylthio-9-anthracenecarbaldehyde and 2-methyl-2-amino-1,3-propanediol (Aldrich) gave 2-((10-ethylthio-9-anthracenylmethyl)amino)-2-methyl-1,3-propanediol hydrochloride, mp 201°–202°, (EtOH/Et$_2$O), (C, H, Cl, N, S).

EXAMPLE 21
2-((10-(2-Hydroxyethylthio)-9-anthracenylmethyl)amino)-2-methylpropanediol hydrochloride

A.
10-((2-Hydroxyethyl)thio)-9-anthracenecarbaldehyde

Using the procedure described in 6A (except that the alkylation reaction was run for 1 h at 65°), 10-chloro-9-anthracenecarbaldehyde (Aldrich) and 2-iodoethanol (Aldrich) gave 10-((2-hydroxyethyl)thio-9-anthracenecarbaldehyde mp 103°–104°, (PhCH$_3$/hexane), (C, H, S).

B.
2-((10-(2-Hydroxyethylthio)-9-anthracenylmethyl)amino)-2-methyl-1,3-propanediol hydrochloride Using the reductive amination procedure described in 1, 10((2-hydroxylethyl)thio)-9-anthracenecarbaldehyde and 2-methyl-2-amino-1,3-propanediol (Aldrich) gave 2-((10-(2-hydroxyethylthio)-9-anthracenylmethyl)amino)-2-methyl-propanediol hydrochloride, mp 199°–200° (dec), (EtOH/Et$_2$O), (C, H, Cl, N, S).

EXAMPLE 22
2-((2-tert-Butyl-10-chloro-9-anthracenylmethyl)amino)-2-methyl-1,3-propanediol hydrochloride A. 2-tert-Butyl-10-chloro-9-anthracenecarbaldehyde and 3-tert-butyl-10-chloro-anthracenecarbaldehydes 2-tert-Butylanthraquinone (Chemical Dynamics Corporation, P.O. Box 395, 3001 Hadley Road, South Plainfield, N.J., 07080) was reductively formylated using the procedure of V. I. Rogovik et. al., *Zh. Org. Khim.* 3 1315 (1967) to give a mixture (~1:1) of 2- and 3-tert-butyl-10-chloro-9-anthracenecarbaldehydes which were separated by preparative HPLC using the shave/recycle technique to obtain 2-tert-butyl-10-chloro-9-anthracenecarbaldehyde mp 126°–129°, (PhCH$_3$/CH$_3$OH), (C, H, Cl), and 3-tert-butyl-10-chloro-9-anthracenecarbaldehyde mp 143°–147°, (PhCH$_3$/CH$_3$OH), (C, H, Cl).

B.
2-tert-Butyl-10-chloro-9-anthracenylmethyl)amino)-2-methyl-1,3-propanediol hydrochloride Using the reductive amination procedure described in 1, 2-tert-butyl-10-chloro-9-anthracenecarbaldehyde and 2-methyl-2-amino-1,3-propanediol (Aldrich) gave 2-((2-tert-butyl-10-chloro-9-anthracenylmethyl)amino)-2-methyl-1,3-propanediol hydrochloride.¼H$_2$O mp 249°–250° (dec), (EtOH/Et$_2$O), (C, H, Cl, N).

EXAMPLE 23
2-((10-Chloro-9-anthracenylmethyl)amino)-2-hydroxymethyl-1,3-propanediol hydrochloride Using the reductive amination procedure described in 1, 10-chloroanthracene-9-carbaldehyde (Aldrich) and tris(hydroxymethyl)aminomethane (Aldrich) gave 2-((10-chloro-9-anthracenylmethyl)amino)-2-hydroxymethyl-1,3-propanediol hydrochloride, mp 251°–254° (dec), (EtOH/Et$_2$O), (C, H, Cl, N).

EXAMPLE 24
2-((10-(2-Hydroxyethyloxy)-9-anthracenylmethyl)amino)-2-methyl-1,3-propanediol hydrochloride

A.
10-(2-Hydroxyethyloxy)-9-anthracencecarbaldehyde

A 3-L 2-neck flask fitted with thermometer, condenser, stirring bar, N$_2$ line and bubbler was charged with KOtBu (MCB Manufacturing Chemists, Inc., 2909 Highland Ave., Cincinnati, OH, 45212, 25 g, 0.22 mol), ethyleneglycol (1500 mL) and 10-chloro-9-anthraldehyde (Aldrich, 50 g, 0.207 mol). The mixture was stirred at 100° for 1.5 h. An additional 5 g (45 mmol) of KOtBu was added and the stirring continued for an additional 0.5 h. The reaction mixture was cooled and poured into 1500 mL of cold H$_2$O, stirred for 10 minutes before the precipitate was collected by filtration. The yellow solid was dissolved in 1 L of CH$_2$Cl$_2$ and passed through a 100 g plug of SiO$_2$ using CH$_2$Cl$_2$ (9 L). The CH$_2$Cl$_2$ contained impurities only and was discarded. The desired material was then eluted with EtOAc (12 L). The appropriate fractions were combined and the solvent removed to give after drying at 50° 10-(2-hydroxyethyloxy)-9-anthracenecarbaldehyde 28.82 g (53%), mp 142°–144°, (CH$_2$Cl$_2$/hexane), (C, H).

B.
2-((10-(2-Hydroxyethyloxy)-9-anthracenylmethyl)amino)-2-methyl-1,3-propanediol hydrochloride Using the reductive amination procedure outlined in 1, 10(2-hydroxyethyloxy)-9-anthracenecarbaldehyde and 2-methyl-2-amino-1,3-propanediol (Aldrich) gave 2-((10-(2-hydroxyethyloxy)-9-anthracenylmethyl)amino)-2-methyl-1,3-propanediol hydrochloride.½H$_2$O.1/10 EtOH mp 179°–181° (dec), (EtOH/Et$_2$O), (C, H, N, Cl).

EXAMPLE 25
2-((10-Ethoxy-9-anthracenylmethyl)amino)-2-methyl-1,3-propanediol hydrochloride

A. 10-Ethoxy-9-anthracenecarbaldehyde

Using the procedure outlined in 11A, except that NaOEt (Aldrich)/EtOH was used instead of NaOCH$_3$/CH$_3$OH, 10-chloro-9-anthraldehyde (Aldrich) gave 10-ethoxy-9-anthracenecarbaldehyde mp 88°–90°, (CH$_2$Cl$_2$/hexane) (C, H).

B.
2-((10-Ethoxy-9-anthracenylmethyl)amino)-2-methyl-1,3-propanediol hydrochloride Using the reductive amination procedure outlined in 1, 10-ethoxy-9-anthracenecarbaldehyde and 2-methyl-2-amino-1,3-propanediol (Aldrich) gave 2-((10-ethoxy-9-anthracenylmethyl)amino)-2-methyl-1,3-propanediol hydrochloride mp 229°–230° (dec), (EtOH/Et$_2$O), (C, H, Cl, N).

EXAMPLE 26
2-((10-Benzoyloxy-9-anthracenylmethyl)amino)-2-methyl-1,3-propanediol hydrochloride Using the reductive amination outlined in 1, 10-benzoyloxy-9-anthracenecarbaldehyde, prepared by the method of L. Nedelec and J. Riguady, *Bull. Soc. Chim. Fr.* 1204 (1960) and 2-methyl-2-amino-1,3-propanediol (Aldrich) gave 2-((10-benzoyloxy-9-anthracenylmethyl)amino)-2-methyl-1,3-propanediol hydrochloride, mp 234°-235° (dec), (EtOH/Et$_2$O), (C, H, Cl, N).

EXAMPLE 27

2-((10-Butoxy-9-anthracenylmethyl)amino)-2-methyl-1,3-propanediol hydrochloride

A. Alkylation of Anthrone

A 2 L 2-neck flask fitted with condenser, stirring bar, addition funnel and N$_2$ line was charged with anthrone (Aldrich, 100 g, 0.515 mol) and 500 mL of EtOH. To the mixture was added quickly a solution containing KOH (Mallinckrodt (85%), 35 g, 0.53 mol) dissolved in 250 mL of EtOH/H$_2$O (5:1). The resulting deep red solution was warmed to 60°. BuBr (Fisher, 127.6 g, 0.93 mol) was added dropwise over 1 h to the reaction. The reaction was then stirred at 60° for 16 h. Most of the color disappeared after 3 h leaving a deep yellow solution with precipitate (KBr). The mixture was cooled and filtered. The solvent was removed. The oily dark material was mixed with PhCH$_3$ (100 mL) and applied to a 1000 g plug of SiO$_2$. Fractions of 250 mL were taken using PhCH$_3$ (5 L) as eluting solvent. Appropriate fractions were taken and further purified by preparative HPLC using PhCH$_3$ as eluting solvent and using normal and shave/recycle techniques. From the reaction the following materials were obtained (after separation and purification) in order of elution on SiO$_2$ with PhCH$_3$.

I. 10-Butoxy-9-butylanthracene mp 31°-35°, 9.9 g (6%), (C, H), Rf=0.83

II. 9-Butoxyanthracene mp 86°-87°, (CH$_3$OH), 52.11 g (44%), (C, H), Rf=0.81

III. 10-Dibutyl-9,10-dihydro-9-anthrone mp 108°-109°, isolated after HPLC as an oil which solidified, 4.0 g (4%), (C, H), Rf=0.53

IV. 10-Butyl-9,10-dihydro-9-anthrone isolated as an oil after HPLC, 41.2 g (29%), (C, H), Rf=0.45

Anthrone (Rf=0.35) was discarded isolation during the separations.

B. 10-Butoxy-9-anthracenecarbaldehyde

10-Butoxyanthracene was formylated using DMF as both solvent and electrophile by the procedure of E. Campaigne and W. L. Archer, *J. Amer. Chem. Soc.* 75 989 (1953), affording 10-butoxy-9-anthracenecarbaldehyde mp 65°-67°, (pentane), (C, H).

C.
2-((10-Butoxy-9-anthracenylmethyl)amino)-2-methyl-1,3-propanediol hydrochloride Using the reductive amination procedure outlined in 1, 10-butoxy-9-anthracenecarbaldehyde and 2-methyl-2-amino-1,3-propanediol (Aldrich) gave 2-((10-butoxy-9-anthracenylmethyl)amino)-2-methyl-1,3-propanediol hydrochloride, mp 216°-218° (dec), (EtOH/Et$_2$O), (C, H, Cl, N).

EXAMPLE 28

2-((10-Butyl-9-anthracenylmethyl)amino)-2-methyl-1,3-propanediol hydrochloride

A. 10-Butyl-9-anthracenecarbaldehyde

10-Butyl-9,10-dihydro-9-anthrone (from 27A) was reduced by the procedure described by H. O. House et. al. *J. Org. Chem.* 38 1167 (1973) to give 9-butylanthracene (mp 49° A. Sieglitz and R. Marx, *Ber.* 56 1619 (1923)). This material was formylated by the procedure described in 14A to give to 10-butyl-9-anthracenecarbaldehyde mp 79°, (CH$_2$Cl$_2$/pentane), (C, H), lit. mp 80.5°-81°, R. H. Martin, and L. van Hove, *Bull. Soc. Chim. Belg.* 61 504 (1952).

B.
2-((10-Butyl-9-anthracenylmethyl)amino)-2-methyl-1,3-propanediol hydrochloride Using the reductive amination procedure outlined in 1, 10-butyl-9-anthracenecarbaldehyde and 2-methyl-2-amino-1,3-propanediol (Aldrich) gave 2-((10-butyl-9-anthracenylmethyl)amino)-2-methyl-1,3-propanediol hydrochloride mp 225°-227° (dec), (EtOH/Et$_2$O), (C, H, Cl, N).

ANTITUMOR SCREENING RESULTS

Methods for evaluating the antitumor activity of these compounds are essentially those used in the Tumor Panel by the Developmental Therapeutics Program, Division of Cancer Treatment, National Cancer Institute, A. Goldin, et al., *Methods in Cancer Research*, Vol. XVI, p. 165, Academic Press (1979). Some modifications, in dose level and schedule have been made to increase the testing efficiency.

EXAMPLE 29

Lymphocytic Leukemia P388/0 Test

CD2-F$_1$ mice, of the same sex, weighing within a 3 g range surrounding 20 g, are used for this test. Control and test animals are injected intraperitoneally with a suspension of $\sim 10^6$ viable P388/0 tumor cells on day 0. In each test several dose levels which bracket the LD$_{20}$ for the compound are evaluated; each dose level group contains 6 animals. The test compounds are prepared either in physiologic saline containing 0.05% Tween 80 or distilled water containing 5% dextrose and are administered intraperitoneally on days 1,5, and 9 relative to tumor implant. Doses are on a mg/kg basis according to individual animals' body weights. The day of death for each animal is recorded, the median identified for each group and the ratios of median survival time for treated (T)/control (C) groups are calculated. The criterion for activity is T/C×100≧120%. Results of P388/0 testing are summarized in Table I below.

TABLE I

| Compound of Example | Optimal Dosage (mg/kg) | T/C × 100% (Excluding 30 Day Survivors) |
|---|---|---|
| 1 | 150 | +130 |
| 2 | 77 | +170 |
| 3 | 425 | +228 |
| 4 | 450 | +200 |
| 5 | 94 | +160 |
| 6 | 110 | +265 |
| 7 | 200 | +210 |
| 8 | 165 | +170 |
| 9 | 387 | +190 |
| 10 | 55 | +200 |
| 11 | 120 | +200 |
| 12 | 300 | +225 |
| 13 | 300 | +172 |
| 14 | 350 | +180 |
| 15 | 450 | +200 |
| 16 | 600 | +200 |
| 17 | 450 | +205 |
| 18 | 200 | +215 |
| 19 | 150 | +170 |
| 20 | 281 | +145 |

TABLE I-continued

| Compound of Example | Optimal Dosage (mg/kg) | T/C × 100% (Excluding 30 Day Survivors) |
|---|---|---|
| 21 | 440 | +145 |
| 22 | 450 | +125 |
| 23 | 277 | +140 |

EXAMPLE 30

Lymphocytic Leukemia L1210 Test

The protocol for this test is identical to that for P388/0 except that the number of L1210 cells implanted on day 0 is $10^5$/mouse. The CD2-$F_1$ mouse strain is used and the criterion for activity is T/C×100>125%. Results of L1210 testing are summarized in Table II below.

TABLE II

| Compound of Example | Optimal Dosage (mg/kg) | T/C × 100% (Excluding 30 Day Survivors) |
|---|---|---|
| 3 | 300 | +131 |
| 6 | 135 | +206 |
| 7 | 275 | +212 |
| 13 | 400 | +187 |
| 17 | 425 | +187 |

EXAMPLE 31

Melanotic Melanoma B16

B6C3-$F_1$ mice of the same sex, weighing within a 3 g range surrounding 20 g, are used for this test. A suspension of B16 cells is prepared from a non-necrotic portion of solid tumor tissue obtained from a passage mouse. One gram of tumor is homogenized in 9 mL ice-cold Earle's salts solution and filtered through 100 mesh screen to remove debris. 0.5 mL of the resulting brei is injected intraperitoneally to each animal. Dosing is carried out as in the P388/0 and L1210 tests. Days of death are recorded for a 60 day period and T/C ratio calculated as in the P388/0 and L1210 tests. The criterion for activity is T/C×100>125%. The results of B16 testing are summarized below in Table III.

TABLE III

| Compound of Example | Optimal Dosage (mg/kg) | T/C × 100% (Excluding 30 Day Survivors) |
|---|---|---|
| 3 | 400 | +150 |
| 6 | 135 | +175 |
| 7 | 175 | +197 |
| 13 | 300 | +200 |
| 17 | 300 | +163 |

EXAMPLE 61

Formulation Examples

| A. TABLET | |
|---|---|
| Compound of Formula I | 500.0 mg |
| Pregelatinized Corn Starch | 60.0 mg |
| Sodium Starch Glycolate | 36.0 mg |
| Magnesium Stearate | 4.0 mg |

The compound of formula (I) is finely ground and intimately mixed with the powdered excipients, pregelatinized corn starch and sodium starch glycolate. The powders are wetted with purified water to form granules. The granules are dried and mixed with the magnesium stearate. The formulation is then compressed into tablets weighing approximtely 600 mg each.

| B. TABLET | |
|---|---|
| Compound of formula (I) | 500.0 mg |
| Corn Starch | 70.0 mg |
| Lactose | 83.8 mg |
| Magnesium Stearate | 4.2 mg |
| Polyvinylpyrrolidone | 14.0 mg |
| Stearic Acid | 28.0 mg |

The compound of formula (I) is finely ground and intimately mixed with the powdered excipients, corn starch and lactose. The powders are wetted with a solution of polyvinylpyrrolidone dissolved in purified water and denatured alcohol to form granules. The granules are dried and mixed with the powdered stearic acid and magnesium stearate. The formulation is then compressed into tablets weighing approximtely 700 mg each.

| C. CAPSULES | |
|---|---|
| Compound of formula (I) | 500.0 mg |
| Corn Starch | 50.0 mg |
| Magnesium Stearate | 3.0 mg |

The finely divided compound of formula (I) is mixed with powdered corn starch and wetted with denatured alcohol to densify the powder. The dried powder is mixed with stearic acid and filled into hard-shall gelatin capsules.

| D. SYRUP | |
|---|---|
| Compound of formula (I) | 250.0 mg |
| Ethanol | 250.0 mg |
| Glycerin | 500.0 mg |
| Sucrose | 3,500.0 mg |
| Flavoring Agent | q.s. |
| Coloring Agent | q.s. |
| Preserving Agent | 0.1% |
| Purified Water q.s. to | 5.0 ml |

The compound of formula (I) is dissolved in the ethanol, glycerin, and a portion of the purified water. The sucrose and preserving agent are dissolved in another portion of hot purified water, and then the coloring agent is added and dissolved. The two solutions are mixed and cooled before the flavoring agent is added. Purified water is added to final volume. The resulting syrup is thoroughly mixed.

| E. IV INJECTION | |
|---|---|
| Compound of formula (I) | 5.0 mg |
| Glycerin | q.s. for isotonicity |
| Preservative | 0.1% |
| Hydrochloric Acid or Sodium Hydroxide | as needed for pH adjustment |
| Water for Injection | q.s. to 1 ml |

The compound of formula (I) and preservative is added to the glycerin and a portion of the water for injection. The pH is adjusted with hydrochloric acid or sodium hydroxide. Water for injection is added to final volume and solution is complete after thorough mixing. The solution is sterilized by filtration through a 0.22 micrometer membrane filter and aseptically filled into sterile 10 ml ampules or vials.

What is claimed is:

1. A pharmaceutical composition in the form of a tablet or capsule containing or a 2-((10-(2-hydroxyethyloxy)-9-anthracenylmethyl)amino)-2-methyl-1,3-propanediol or a pharmaceutically acceptable salt thereof together with a pharmaceutically acceptable carrier therefor.

2. A tablet or capsule for medicinal use containing 2-((10-(2-hydroxyethyloxy)-9-anthracenylmethyl)amino)-2-methyl-1,3-propanediol hydrochloride together with a pharmaceutically acceptable carrier therefor.

3. A sterile pharmaceutical parenteral preparation comprising 2-((10-(2-hydroxyethyloxy)-9-anthracenylmethyl)amino)-2-methyl-1,3-propanediol or a pharmaceutically acceptable salt thereof together with a pharmaceutically acceptable solvent therefor.

4. A sterile pharmaceutical preparation comprising 2-((10-(2-hydroxyethyloxy)-9-anthracenylmethyl)amino)-2-methyl-1,3-propanediol hydrochloride and a pharamceutically acceptable solvent therefor.

5. The method of reducing the number of cells of a susceptible tumor which comprises contacting said susceptible tumor cells with a tumor reducing amount of the compound 2-((10-(2-hydroxyethyloxy)-9-anthracenylmethyl)amino)-2-methyl-1,3-propanediol or a pharmaceutically acceptable salt thereof.

6. The method of reducing the number of cells of a susceptible tumor which comprises contacting said susceptible tumor cells with a tumor reducing amount of 2-((10-(2-hydroxyethyloxy)-9-anthracenylmethyl)amino)-2-methyl-1,3-propanediol hydrochloride.

7. A pharmaceutical composition in a form for parenterial or oral use containing 2-((10-(2-hydroxyethyloxy)-9-anthracenylmethyl)amino)-2-methyl-1,3-propanediol or a pharmaceutically acceptable salt thereof together with a pharmaceutically acceptable carrier therefor.

* * * * *